United States Patent [19]

Liebeschuetz et al.

[11] Patent Number: 5,292,743

[45] Date of Patent: Mar. 8, 1994

[54] FUNGICIDAL COMPOSITIONS, FUNGICIDAL COMPOUNDS, THEIR PRODUCTION AND USE

[75] Inventors: John W. Liebeschuetz, Wantage, Great Britain; Michel J. Jung, Tradate, Italy; Thomas A. K. Smith, Huntington, Great Britain

[73] Assignee: DowElanco, Indianapolis, Ind.

[21] Appl. No.: 847,017

[22] PCT Filed: Oct. 9, 1990

[86] PCT No.: PCT/GB90/01555

§ 371 Date: Apr. 8, 1992

§ 102(e) Date: Apr. 8, 1992

[51] Int. Cl.$^5$ .................. A01N 43/54; A01N 55/00
[52] U.S. Cl. ........................................ 514/275; 514/63
[58] Field of Search ................................ 514/275, 63

[56] References Cited

U.S. PATENT DOCUMENTS

| 2,988,478 | 6/1961 | Gordon | 167/33 |
|---|---|---|---|
| 4,396,617 | 8/1983 | Dolman et al. | 514/275 |
| 4,992,438 | 2/1991 | Ito et al. | 514/275 |

FOREIGN PATENT DOCUMENTS

0001663  5/1979  European Pat. Off.
0323757  7/1989  European Pat. Off.

OTHER PUBLICATIONS

Chemical Abstracts, vol. 110:212684r, No. 23, Jun. 5, 1989, Glushkov, R. G. et al., "Synthesis and pharmacologic study of novel substituted guanidines and 2-amino-2-imidazolines".

Primary Examiner—Allen J. Robinson
Attorney, Agent, or Firm—S. Preston Jones; Kenneth L. Loertscher

[57] ABSTRACT

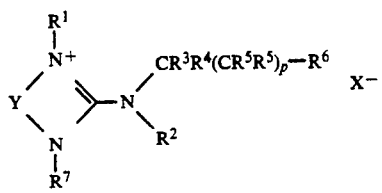

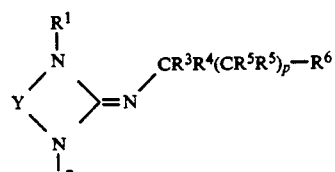

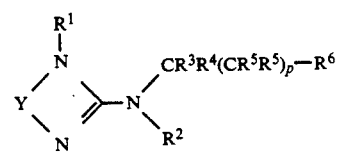

Agricultural fungicidal compositions comprising compounds of formula (I-A), (I-B) or (I-C), wherein $R^1$ and $R^7$ are each independently hydrogen or $C_1$-$C_3$ alkyl, $R^2$ is hydrogen or $C_1$-$C_6$ alkyl, $R^3$ and $R^4$ independently, and each $R^5$ independently are hydrogen or $C_1$-$C_4$ alkyl, $R^6$ is a cyclohexyl group or a monocyclic or bicyclic aromatic group, substituted with from 1 to 5 groups of the formula $R^8$, wherein $R^8$ is halogen, a $C_1$-$C_{10}$ alkyl group, a $C_1$-$C_{10}$ alkoxy group, a tri-$C_1$-$C_4$-alkylsilyl group, or a phenoxy, phenyl, phenyl-$C_1$-$C_2$-alkylene, or phenyl-$C_2$-alkenylene group, each optionally substituted on the phenyl or phenoxy group with one or more of halogen atoms, $C_1$-$C_6$ alkyl or $C_1$-$C_6$ alkyl or $C_1$-$C_6$ alkoxy group, trihalomethyl groups, phenyl groups, or phenoxy groups, p is 0, 1 or 2, Y is a group of the formula —$(CR^9R^9)_n$—, wherein n is 2, 3, or 4, each $R^9$ independently is hydrogen or $C_1$-$C_4$ alkyl and X is a suitable counter-ion, together with an agriculturally acceptable carrier or diluent, and novel fungicidal compounds of formula (I-A), (I-B), or (I-C), wherein p is 1 or 2 and n is 3 or 4.

13 Claims, No Drawings

FUNGICIDAL COMPOSITIONS, FUNGICIDAL COMPOUNDS, THEIR PRODUCTION AND USE

This invention relates to novel chemical compounds having fungicidal activity, and in particular to such compounds containing a guanidine group and to the use of these and other compounds as fungicides.

Certain substituted guanidines are disclosed without reference to antifungal activity in an article by Glushkov and Nikolaeva (Chem Abst. Vol 110, No. 212684r) and in Dutch Patent No. 6510117.

Many substituted guanidines are known to have antifungal and antibacterial activity. A detailed review of the antifungal activity of such compounds is to be found in International Pest Control, November/December-1986, p.p.148-155 (H. R. Hudson, I. A. O. Ojo, and M. Pianka).

Fungicidally active compounds containing a guanidine-type grouping compounds are also disclosed, for example in U.S. Pat. No. 2,988,478.

The present invention provides the use as a fungicide of compounds of the formula

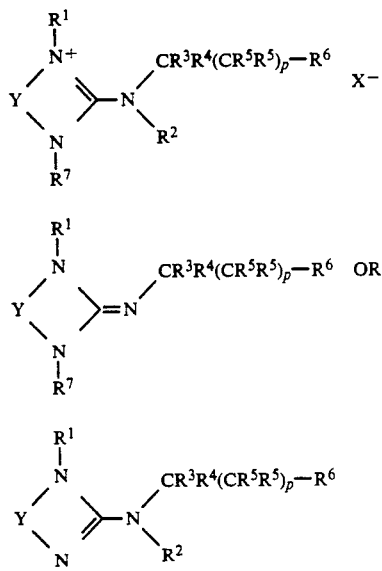

wherein $R^1$ and $R^7$ are each independently hydrogen or $C_1$-$C_3$ alkyl, $R^2$ is hydrogen or $C_1$-$C_6$ alkyl, $R^3$ and $R^4$ independently and each $R^5$ independently are hydrogen or $C_1$-$C_4$ alkyl, $R^6$ is a cyclohexyl group or a monocyclic or bicyclic aromatic group (for example phenyl or naphthalenyl) substituted with from 1 to 5 groups of the formula $R^8$, wherein $R^8$ is halogen, a $C_1$-$C_{10}$ alkyl group, preferably $C_3$-$C_4$ alkyl, more preferably t-butyl, a $C_1$-$C_{10}$ alkoxy group, a trialkylsilyl group, or a phenyl, phenoxy, phenyl $C_1$-$C_2$ alkylene, or phenyl alkenylene group, optionally substituted on the phenyl or phenoxy group with from 1 to 5 halogen atoms, $C_1$-$C_6$ alkyl or $C_1$-$C_6$ alkoxy groups, trihalomethyl groups, phenyl groups or phenoxy groups, p is 0, 1 or 2

Y is a group of the formula $-(CR^9R^9)_n-$, wherein n is 2, 3, or 4, each $R^9$ independently is hydrogen or $C_1$-$C_4$ alkyl, and $X^-$ is a suitable counter-ion. The invention also provides fungicidal compositions which contain such compounds, particularly together with an agriculturally acceptable carrier or diluent.

A number of compounds of formula I-A, I-B and I-C are novel, particularly those wherein p is 1 or 2 and n is 3 or 4. Accordingly, the invention also provides such novel compounds.

It will of course be appreciated that although the compounds of formulae I-A, I-B and I-C are illustrated as containing simple double bonds, in practice considerable delocalisation of the double bond structure will take place over the three nitrogen atoms of the compound. The compounds of the invention contain three basic nitrogen atoms, and thus can exist either in the form of the free base (formulae I-B and I-C), or a salt (formula I-A), for example a quaternary salt or an acid addition salt. The compound can thus exist in tautomeric forms, all of which are within the scope of the present invention.

$R^1$ and $R^7$ are preferably each hydrogen, methyl or ethyl more preferably hydrogen, and $R^2$ is preferably hydrogen or methyl, more preferably hydrogen.

Y is preferably a group of the formula $-(CR^9R^9)_3-$, wherein $R^9$ is as defined above (preferably hydrogen or methyl), more preferably a group of the formula $-(CH_2)_3-$, or $-CHMeCH_2CHMe-$.

Each of groups $R^4$ and $R^5$ are preferably hydrogen, group $R^3$ is preferably methyl, and p is preferably 1.

The group $R^6$ is preferably a substituted phenyl group, more preferably a 4-t- butylphenyl group or 4-trimethylsilylphenyl.

The ring containing the guanidine group is preferably six membered, i.e. n in the definition of Y is preferably 3.

The terms alkyl, alkoxy, alkylene, alkenylene and the like, as used herein, are intended to include within their scope both straight and branched groups, and the terms alkenyl, alkenylene and the like are intended to include groups containing one or more than one double bonds. The term halogen and halo as used herein include chlorine, bromine, fluorine and iodine. It will be appreciated that certain combinations of substituent groups for compounds which fall within the definition of formula I-A, I-B and I-C given above will be impossible to prepare for steric and other chemical reasons. Such compounds are not included within the scope of the invention.

The anion $X^-$ in formula I-A may be any anion addition salt capable of forming an acid, for example chloride, bromide, acetate, stearate, benzoate or dodecylbenzenesulphonate, the chloride being preferred.

The compounds of formula I-A, I-B and I-C may be prepared by reacting a compound of the formula

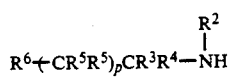

with a salt of the formula

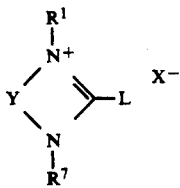

wherein $R^1$ to $R^6$, Y, X and p are as defined above, and L is a suitable leaving group, for example an alkylthio group, preferably at a temperature of from 50° to 200° C. The reaction may be carried out in a suitable organic solvent for example an alkanol such as n-pentanol, or in the absence of solvent.

L is preferably an alkylthio group.

The compounds of formula I-A, I-B and I-C may also be prepared by reducing a compound of formula

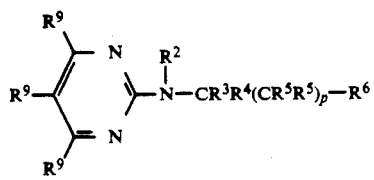

V preferably utilising hydrogen and a metallic catalyst. The reaction may be carried out at atmospheric temperature and pressure in a polar solvent, in the presence of an acid. The compound of formula V may be prepared by reacting a compound of the formula

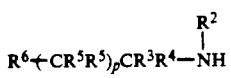

with a compound of the formula

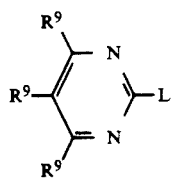

IV wherein $R^2$ to $R^6$ and each $R^9$ independently, is as defined above, and L is a suitable leaving group. The reaction between compound II and compound III is preferably carried out in a polar solvent at a temperature of from 50° to 200° C., in the presence of a base. Compounds of the formula II may generally be prepared by the reaction of a compound of the formula

with a compound of the formula:

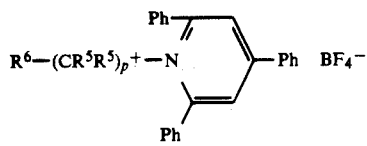

followed by reduction of the nitro group, preferably employing a metal hydride such as LiAlH$_4$, and when $R^2$ is alkyl, alkylation with an alkylating agent, for example a haloalkane. Compound VI may be prepared according to Katrizky, de Ville and Patel (J.C.S. Chem. Comm. 1979, 602) from a compound of formula

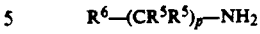

and 2,4,6,-triphenylpyrilium tetrafluoroborate.

Alternatively and preferably, compounds of formula I-B, wherein certain of the $R^5$ groups are restricted to hydrogen, may be prepared by the reaction of a compound of the formula

with a compound of the formula

preferably in the presence of a mild base at a temperature of from 25° to 150° C., followed by reduction of the nitro group and the double bond. The reduction may be carried out, for example using a metal hydride such as LiAlH$_4$, at a temperature of from −80° to 100° C.

The compounds of formula I-A, I-B and I-C may be used as fungicides in particular for agricultural use, against a wide range of pathogens, for example Ascomycetes, Eumycetes and Fungi Imperfecti, in a protectant or eradicant fashion, and exhibit low phytotoxcicity to crops, in particular cereal and broadleaf crops. In particular, the compounds in accordance with the invention may be applied to the roots, seeds, or foliage of barley and other plants, for the control of various fungi, without damaging their commercial value. In particular the compounds of the present invention effectively control a variety of undesirable fungi which infest useful plant crops. Many of the compounds are particularly effective against members of the i) Deuteromycotina such as *Septoria nodorum* (glume blotch of cereals), *Pyricularia oryzae* (rice-blast), *Botrytis cinerea* (grey mould of grapes and *Fusarium Oxysporum* (various wilt diseases), ii) Ascomycotina such as *Pyrenophora teres* (net-blotch) and *Erysiphe graminis* (powdery mildew), and iii) Basidiomycotina such as *Puccinia recondita* (leaf rust).

The compounds can be applied to the seeds, roots or foliage of cereals or other plants and will kill or control the growth of various fungi without damaging the commercial value of the said plants.

Where the acid addition salt is employed, the improved water solubility (especially of the chloride) also allows the preparation of solutions (in water or organic solvents) in which, at use rate, the addition salt is completely soluble in the spray dilution.

At least utilising the preferred embodiments of the invention a single application of the compounds can provide a residual control of powdery mildew diseases over an extended period. Also, the compounds can be effective in eliminating established barley powdery mildew infestation. Furthermore, many compounds have been found to be translocated in plants and, thus, can provide a systemic protection against powdery mildew.

The compounds of the invention may also find application as non-agricultural fungicides for example in medicine as antimycotics against organisms such as *Candida albicans, Candida spp, Trichophyton spp, Asper-*

*gillus spp*, *Microsporum spp* and *Sporothrix spp*, and also as agents against parasites such as Leishmania.

As indicated above, the invention includes within its scope fungicidal compositions comprising a fungicidally effective amount of a compound of formula I-A, I-B or I-C together with an inert carrier or diluent. Such compositions may be in the form of a liquid, powder, dust or granular composition containing one or more of the active compounds in and one or more inert, non-phytotoxic materials, known in the art as agricultural adjuvants and/or carriers, in solid or liquid form. Thus, for example, the active compound(s) can be admixed with one or more additives including water or other liquid carriers such as organic solvents, and petroleum distillates, surface active dispersing agents, and finely divided inert solids.

In such compositions, the active ingredients are generally present in a concentration of from 2 per cent to about 95 per cent by weight preferably from 10 per cent to 95 per cent by weight and most advantageously 10 per cent to 75 per cent by weight. The compound can be employed in the form of a solution, a diluted flowable compositions or a wettable powder composition containing 2 to 10,000 ppm of active ingredient. Preferably 10 to 600 ppm are employed.

When the carrier contains a surface active agent, from about 0.1 to about 20 per cent by weight of the active ingredient is advantageously employed. Depending upon the concentration in the composition, such augmented compositions are adapted to be employed for the control of the undesirable fungi or employed as concentrates and subsequently diluted with additional inert carrier, e.g. water, to produce the ultimate treating compositions.

In general, good results can be obtained with liquid compositions containing from about 0.0001 to about 2.0 per cent by weight of the active compound in the final diluted form. With dusts, good results can usually be obtained with compositions containing from about 0.1 to about 2.0 per cent or more by weight of active compound. Where the compositions are to be applied to foliage of plants, it is preferred that the toxicant be present in an amount not to exceed about 0.8 per cent in liquid compositions and about 1.0 per cent in dusts.

In terms of hectarage application, good controls of powdery mildews can be obtained when the active ingredients are applied to growing plants at a dosage of from about 0.004 to about 4 kg/hectare. When employed as fungicides for the treatment of seeds or non-living substrates, from about 0.1 to about 100 gram of active ingredient per kilogram of substrate is an effective dose.

In the preparation of dust, or wettable powder compositions, the toxicant products can be compounded with any of the finely divided solids, such as prophyllite, talc, chalk, gypsum, fuller's earth, bentonite, attapulgite, starch, casein, gluten, or the like. In such operations, the finely divided carrier is ground or mixed with the toxicant or wet with a solution of the toxicant in a volatile organic solvent. Also, such compositions when employed as concentrates can be dispersed in water, with or without the aid of dispersing agents to form spray mixtures. Dust compositions are advantageously employed when treating seeds.

Granular formulations are usually prepared by impregnating a solution of the toxicant in a volatile organic solvent onto a bed of coarsely divided attapulgite, bentonite, diatomite, or the like.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions which may optionally contain water miscible organic co-solvents to improve the physical properties of the formulation. In such compositions, the carrier comprises an aqueous emulsion, i.e., a mixture of inert water-immiscible solvent and optional water miscible organic co-solvent, emulsifying agent, and water.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxide or mixtures of ethylene and propylene oxides such as the ethoxylated alkyl phenols and carboxylic esters solubilized with the polyol or polyoxyalkylene. Cationic emulsifiers include quaternary ammonium compounds and fatty amines. Anionic emulsifiers include the oil-soluble salts (e.g., calcium) of alkylaryl sulphonic acids, oil soluble salts or sulphated polyglycol ethers and appropriate salts of phosphated polyglycol ether.

Representative organic liquids which can be employed in preparing the emulsifiable concentrates of the present invention are the aromatic liquids such as xylene; propyl benzene fractions; or mixed naphthalene fractions; mineral oils substituted aromatic organic liquids such as dioctyl phthalate; kerosene; butene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface active dispersing agents are usually employed in liquid compositions and in the amount of from 0.1 to 20 per cent by weight of the combined weight of the dispersing agent and active compound. The active compositions can also contain other compatible additives, for example, plant growth regulators and other biologically active compounds used in agriculture.

In particular, the active compositions may contain adjuvant surfactants to enhance the deposition, wetting and penetration of the composition onto the target crop and organism. These adjuvant surfactants may optionally be employed as a component of the formulation or as a tank mix. The amount of adjuvant surfactant will vary from 0.01 per cent to 1.0 per cent v/v based on a spray-volume of water, preferably 0.05 to 0.5 per cent. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

In such embodiments, the compounds of the present invention or compositions containing the same, can be advantageously employed in combination with one or more additional pesticidal compounds. Such additional pesticidal compounds may be insecticides, nematocides, miticides, arthropodicides, or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additive. The compounds in combination can generally be present in a ratio of from 1:100 to 100:1.

The exact amount of the active material to be applied is dependent not only on the specific active material being applied, but also on the particular action desired, the fungal species to be controlled and the stage of growth thereof as well as the part of the plant to be contacted with the toxic active ingredient. Thus, all of the active ingredients of the present invention and compositions containing the same may not be equally effective at similar concentrations or against the same fungal species.

The compounds in accordance with the invention may be applied in the form of any of the generally used formulation types, for example as solutions, dusts, wettable powders, flowable concentrates, or emulsifiable concentrates The invention includes within its scope a method for the control or prevention of fungal attack, which method comprises applying to the locus of the fungus, or to a locus in which the infestation is to prevented, (for example applying to cereal grain plants), a fungicidal amount of one or more of the compounds.

A number of preferred embodiments of the invention are illustrated in the following Examples.

EXAMPLE 1

Preparation of
N-(1-(4-t-butylphenyl)prop-2-yl)-N'N''-trimethylene guanidinium chloride

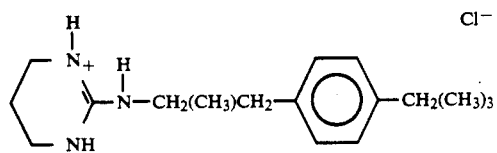

a) Preparation of 1-(4-t-butylphenyl) -2-nitroprop-1-ene 12.4 g of 4-t butylbenzaldehyde, 30 ml of nitroethane and 2.9 g of ammonium acetate were refluxed together under nitrogen for 4 hours. The nitroethane was distilled off and the residue taken up in ethylacetate. This was washed twice with water, dried, filtered and the solvent evaporated off. The residue was distilled at 90° C. (0.5 torr) Hg to afford a lemon yellow oil. Elemental analysis indicated the following:- C=71.3%; H=7.85%; N=6.5%; (calculated, C=71.2%; H=7.80%; N=6.4%).

b) Preparation of 1-(4-t butylphenyl)propan-2-amine 7.6 g of the nitroolefin prepared in (a) above was dissolved in 150 ml dry diethylether and added dropwise to 10 g of lithium aluminium hydride in 300 ml diethylether under nitrogen with stirring. On completion of addition the mixture was refluxed for 24 hours. 35 ml of triethanolamine was added over 2 hrs with cooling and then 9 ml water added dropwise. The mixture was stirred for 2 hrs and the resulting suspension of sandy consistency filtered. The solids collected were washed with diethylether and the washings combined with the organic solution. This was washed, dried with MgSO4 filtered, the solvent evaporated under reduced pressure and the residue distilled at 65° C., (0.44 torr) to afford 5.4 g of an oil. NMR and IR spectra were consistent with the title compound c) Preparation of 2-(1-(4-t butylphenyl) propan-2-amino)pyrimidine 4.5 g of 1-(4-t-butylphenyl)-propan-2-amine, 2.68 g of 2-chloropyrimidine and 3.05 g of ethyldiisopropylamine, all in 40 ml pentanol, were refluxed under nitrogen for 24 hours. The solvent was distilled off at reduced pressure and the residue taken up in dichloromethane and washed three times with water. The organic layer was dried with MgSO4, filtered and the solvent removed under reduced pressure. The residue was chromatographed on silica gel, EtOAc/hexane to yield 3.4 g of a yellowish solid. Elemental analysis indicated the following;

C = 75.5%; H = 8.5%; N = 14.2%
(calculated, C = 75.8%; H = 8.6%; N = 15.6%).

d) 1 g of 2-(1-(4-t-butylphenyl)propan-2-amino) pyrimidine was dissolved in 25 cc absolute ethanol, and 150 mg of 10% palladium on charcoal and 1 ml of 2N hydrochloric acid were added. The mixture was agitated and hydrogenated at atmospheric pressure until hydrogen uptake ceased. The mixture was filtered and the solvent removed under reduced pressure to afford 1 g of a gum. NMR and IR spectrocopy of the product were consistent with the expected structure for the title compound of Example 1.

EXAMPLE 2

Preparation of
N-(2-(4-t-butylphenyl)ethyl-N'N''-trimethylene guanidinium chloride

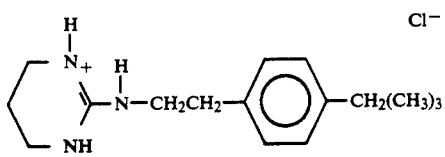

4-t butylphenethylamine was prepared in a manner analogous to that used in steps (a) and (b) in Example 1, except that nitromethane was used in place of nitroethane in step (a).

1.2 g of 4-t-butylphenethylamine and 1.6 g S-ethyl-N,N'-trimethylenethiuronium bromide were dissolved in 9 ml ethanol and refluxed for 24 hours. The solvent was evaporated off and the residue chromatographed on silica (CHCl3/EtOH/AcOH) to afford 1 g of a gum. Elemental analysis indicated the following C=55.2%; H=7.75%; N=11.6% (calculated, C=56.5%; H ; 7.70; N=12.3). NMR and IR spectra were consistent with the expected structure.

EXAMPLES 3 AND 4

N-(1-(4-t-butylphenyl)prop-2- yl)-N',N'''-pent-2,4 diyl guanidinium acetate (Example 3)

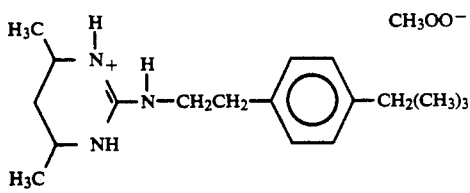

and chloride (Example 4)

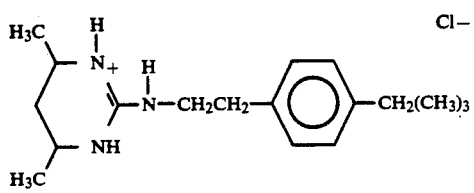

were prepared by methods analogous with those used in Example 1, except that 2-chloro, 4,6 dimethyl pyrimidine was used in place of 2-chloro pyrimidine in step (c), and in Example 5, acetic acid was used in place of hydrochloric acid. NMR and IR spectra were consistent with the expected structure.

EXAMPLE 5

Preparation of N-(1-(4-hexylphenyl)prop-2-yl)-N', N''-trimethyleneguanidinium chloride

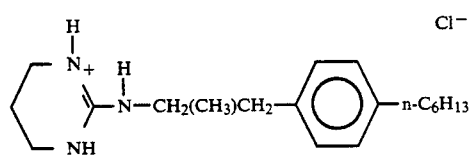

The preparation was carried out in a manner analogous to that used in Example 1, except that 4-hexylbenzaldehyde was used instead of 4-t-butyl benzaldehyde. NMR and IR spectra were consistent with the expected structure.

EXAMPLE 6

Preparation of N-(1-(4-(2-phenylethyl)phenyl)prop-2-yl)-N'N''-trimethylene guanidinium chloride

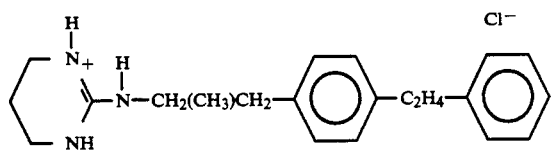

The preparation was carried out in a manner analogous to that used in Example 1, except that 4-styrylbenzaldehyde was used instead of 4-t-butylbenzaldehyde. The double bond of the styryl group was reduced in step (d). NMR and IR spectra were consistent with the expected structure.

EXAMPLE 7

Preparation of N-(1-(4-phenylphenyl)prop-2-yl)-N'N''-trimethylene guanidinium chloride

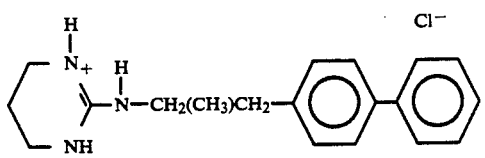

The preparation was carried out in a manner analogous to that used in Example 1, except that 4-phenylbenzaldehyde was used instead of 4-t-butyl benzaldehyde. NMR and IR spectra were consistent with the expected structure.

EXAMPLE 8

Preparation of N-(1-(3-phenoxyphenyl)prop-2-yl)-N'N''-trimethylene guanidinium chloride

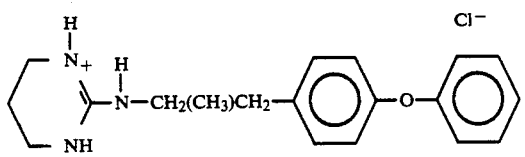

The preparation was carried out in a manner analogous to that used in Example 1, except that 3-phenoxybenzaldehyde was used instead of 4-t-butyl benzaldehyde. Elemental analysis indicated the following C=65.2%; H=6.95%; N=11.7% (calculated, C=65.9%; H=7.00%; N=12.1%). NMR and IR spectra were consistent with the expected structure.

Test Procedures

The compounds of Examples 1 to 8 were tested in accordance with the following in vitro and in vivo test methods.

In Vitro Screen Method

Test compounds are generally dissolved in acetone and made up with distilled water to give a solution with a final concentration of compound of 400 ppm and 10 per cent acetone. 2 ml aliquots of the latter solutions are pipetted into sterile petri dishes, and 18 ml of agar is then added to each dish using an automatic agar plate pourer to give a final concentration of compound of 40 ppm.

Once the agar is set, discs of pathogens are cut from stock agar plates using a cork borer, and placed (pathogen face down) onto the test agar surface. Pathogens used in the primary screen include:

1. *Alternaria brassicola*
2. *Fusarium oxysporum phaseolicola*
3. *Pyrenophora teres*
4. *Botrytis cinerea*
5. *Pyricularia oryzae*
6. *Pseudocercosporella herpotrichoides*.

Three pathogens are placed on each plate. Two replicates of each plate are set up and kept in an incubator at 20° C.

The pathogens on plate 1 are assessed after 5 days and those on plate 2 after 8 days. The diameters of the fungal colonies are measured after the incubation period and compared to the control measurements. Allowing for the diameter of the original disc, percentage inhibition values are then calculated.

In Vivo Screen Method

Compounds are dissolved in acetone or water (as required) and made up with distilled water to give a final concentration of compound of 400 ppm (and 10% acetone where acetone is used).

For each compound 3 replicate plants per pathogen (at the 1 leaf stage for cereals and at least the 2 leaf stage for vines) are sprayed to run off. The plants are allowed to dry at room temperature for 24 hours prior to inoculation.

Untreated control plants and plants sprayed with 10% acetone water or water (as required) are included for each pathogen.

Method for Erysiphe graminis Hordei

Barley cv. Golden Promise is used as the host plant. Seeds are sown 8 per 3" pot (plants approximately 2 weeks old). Spores are blown onto the test plants from the stock plants, which are then incubated at 20° C., relative humidity 70% for 7 days. After a week symptoms are recorded % infection is scored from 3 replicate plants and expressed as a % of acetone/water control plants. % control is then recorded.

Method for Puccinia recondita

Wheat cv. Tonic. Seeds are sown 1 cm deep in 4 rows per plastic tray 60 cm × 30 cm. Seedlings are inoculated at 1-2 leaf stage. 0 05 g of uredospores are put into 100 ml distilled water with a melting agent. This solution is sprayed onto seedlings leaving a fine coverage on the leaves. The plants are then incubated with 100% relative humidity at 15°-20° C. for 4 days.

% infection is scored from 3 replicate plants and expressed as a % of acetone/water control plants. % control is then recorded.

The results are shown in Table 1 and 2 respectively.

TABLE 1

In vitro Biological Evaluation
Per cent Efficacy of Compounds of Examples 1 to 8

| Example Number | Alternaria brassicola | Fusarium oxysporum | Pyrenophora teres | Pseudocercosporella herpotrichoides | Botrytis cinerea | Pyricularia oryzae |
|---|---|---|---|---|---|---|
| 1 | 91 | 64 | 86 | 82 | 100 | 33 |
| 2 | 97 | 40 | 80 | NT | 78 | NT |
| 3 | NT | 70 | 79 | 64 | NT | 63 |
| 4 | NT | 72 | 77 | 45 | NT | 59 |
| 5 | NT | 78 | 78 | 67 | NT | 58 |
| 6 | NT | 88 | 83 | 67 | NT | 74 |
| 7 | NT | 67 | 14 | 50 | NT | 53 |
| 8 | NT | 75 | 38 | 100 | NT | 68 |

NT - Not Tested

TABLE 2

In vitro Biological Evaluation
Per cent Efficacy of Compounds of Examples 1 to 10

| Example Number | Erysiphe graminis | Puccinia recondita | Phytotoxicity (%) |
|---|---|---|---|
| 1 | 100 | NT | 0 |
| 2 | 73 | NT | 0 |
| 3 | 100 | 0 | 0 |
| 4 | 100 | 30 | 0 |
| 5 | 87 | 82 | 0 |
| 6 | 19 | 87 | 0 |
| 7 | 92 | 100 | 0 |
| 8 | 73 | 100 | 0 |

NT - Not Tested

We claim:

1. An agricultural fungicidal composition comprising a fungicidally effective amount of a compound of the formula:

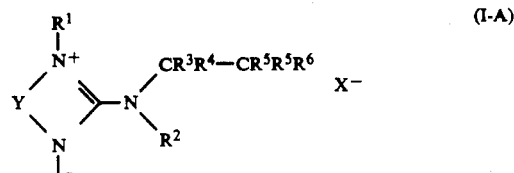

(I-A)

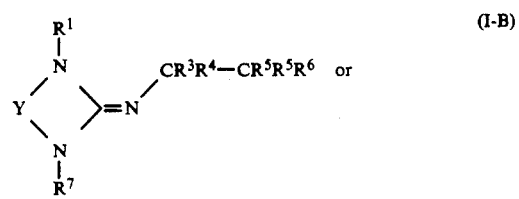

(I-B)

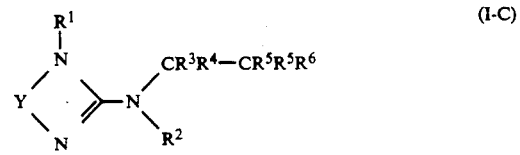

(I-C)

wherein $R^1$ and $R^7$ are each independently hydrogen or $C_1$-$C_3$ alkyl,
$R^2$ is hydrogen or $C_1$-$C_6$ alkyl,
$R^3$ and $R^4$ independently, and each $R^5$ independently are hydrogen or $C_1$-$C_4$ alkyl,
$R^6$ is phenyl or phenyl substituted with from 1 to 5 groups of the formula $R^8$,
$R^8$ is halogen, $C_1$-$C_{10}$ alkyl, $C_1$-$C_{10}$ alkoxy, tri-$C_1$-$C_4$-alkylsilyl, phenoxy, phenyl, phenyl-$C_1$-$C_2$-alkylene, or phenyl-$C_2$-alkenylene, provided that any R8 that includes a phenyl ring may be substituted on the phenyl ring with one or more groups selected from halogen, $C_1$-$C_6$ alkyl, $C_1$-$C_6$ alkoxy, trihalomethyl, phenyl, or phenoxy,
Y is a group of the formula—$(CR^9R^9)_3$—, wherein each $R^9$ independently is hydrogen or $C_1$-$C_4$ alkyl and X is a suitable counter-ion,
together with an agriculturally acceptable carrier.

2. A composition as claimed in claim 1, wherein $R^1$ and $R^7$ are each independently hydrogen, methyl or ethyl.

3. A composition as claimed in claim 2, wherein $R^1$ and $R^7$ are each hydrogen.

4. A composition as claimed in claim 2, wherein Y is a group of the formula

—(CH$_2$)$_3$—, or —CHMeCH$_2$CHMe—.

5. A method for the control or prevention of fungal infestation, which method comprises applying to the locus of the fungus, or in which the infestation is to be prevented, a fungicidally effective amount of the composition as claimed in claim 1.

6. The composition as defined in claim 1 wherein the compound is N-(1-(4-phenyl-phenyl)prop-2-yl)-N',N''-trimethylene guanidinium chloride.

7. The composition as defined in claim 1 wherein the compound is N-(1-(3-phenoxy-phenyl)prop-2-yl)-N',N''-trimethylene guanidinium chloride.

8. The composition as defined in claim 1 wherein the compound is N-(1-(4-(2-phenylethyl)phenyl)prop-2-yl)-N',N''-trimethylene guanidinium chloride.

9. The composition as defined in claim 1 wherein the compound is N-(1-(4-hexylphenyl)prop-2-yl-N',N''-trimethylene guanidinium chloride.

10. The composition as defined in claim 1 wherein the compound is N-(1-(4-t-butylphenyl)prop-2-yl)-N',N''-trimethylene guanidinium chloride.

11. The composition as defined in claim 1 wherein the compound is N-(2-(4-t-butylphenyl)ethyl-N',N''-trimethylene guanidinium bromide.

12. The composition as defined in claim 1 wherein the compound is N-(1-(4-t-butylphenyl)prop-2-yl)-N',N''-pent-2,4-diyl guanidinium acetate.

13. The composition as defined in claim 1 wherein the compound is N-(1-(4-t-butylphenyl)prop-2-yl)-N',N''-pent-2,4-diyl guanidinium chloride.

* * * * *